US008173188B2

(12) United States Patent
Suetsugu

(10) Patent No.: US 8,173,188 B2
(45) Date of Patent: May 8, 2012

(54) METHOD OF CONTROLLING HEATING COOKING APPARATUS

(75) Inventor: Yumiko Suetsugu, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 1127 days.

(21) Appl. No.: 12/027,788

(22) Filed: Feb. 7, 2008

(65) Prior Publication Data

US 2009/0204241 A1 Aug. 13, 2009

(51) Int. Cl.
*G01N 33/02* (2006.01)
*G06F 17/00* (2006.01)

(52) U.S. Cl. .......... 426/231; 426/233; 219/492; 700/89; 700/207; 700/211; 700/296

(58) Field of Classification Search .................. 426/231, 426/233–234, 237, 241, 243, 520, 523; 219/702, 219/705, 707, 708, 715–716, 719, 492; 700/89, 700/207, 211, 296, 300, 305–306
See application file for complete search history.

(56) References Cited

U.S. PATENT DOCUMENTS

| | | | | | |
|---|---|---|---|---|---|
| 3,839,616 | A | * | 10/1974 | Risman | 219/707 |
| 4,097,707 | A | * | 6/1978 | Kobayashi et al. | 219/707 |
| 4,154,855 | A | * | 5/1979 | Buck | 426/243 |
| 4,162,381 | A | * | 7/1979 | Buck | 219/705 |
| 4,181,744 | A | * | 1/1980 | Buck | 426/233 |
| 4,281,022 | A | * | 7/1981 | Buck | 426/233 |
| 4,316,068 | A | * | 2/1982 | Tanabe | 219/705 |
| 4,335,293 | A | * | 6/1982 | Kobayashi et al. | 219/707 |
| 4,336,433 | A | * | 6/1982 | Yokozeki | 219/707 |
| 4,350,860 | A | * | 9/1982 | Ueda | 219/705 |
| 4,376,131 | A | * | 3/1983 | Mori et al. | 426/231 |
| 4,379,964 | A | * | 4/1983 | Kanazawa et al. | 219/492 |
| 4,496,817 | A | * | 1/1985 | Smith | 219/707 |
| 4,814,570 | A | * | 3/1989 | Takizaki | 219/705 |
| 4,841,111 | A | * | 6/1989 | Kokkeler et al. | 219/703 |
| 4,864,088 | A | * | 9/1989 | Hiejima et al. | 219/707 |
| 4,874,928 | A | * | 10/1989 | Kasai | 219/492 |
| 5,155,339 | A | * | 10/1992 | An | 219/492 |
| 5,215,000 | A | * | 6/1993 | Desage et al. | 99/331 |
| 5,395,633 | A | * | 3/1995 | Lee | 426/233 |
| 5,422,465 | A | * | 6/1995 | Kim et al. | 219/710 |

(Continued)

FOREIGN PATENT DOCUMENTS

JP 62-126589 A 6/1987

(Continued)

*Primary Examiner* — Drew Becker
*Assistant Examiner* — Luana Z Long
(74) *Attorney, Agent, or Firm* — Birch, Stewart, Kolasch & Birch, LLP

(57) ABSTRACT

In a method of controlling a heating cooking apparatus, when a generated steam volume at a forced finish time $T_{n-1}$ determined based on a minimum volume-minimum steam curve does not reach a minimum steam volume $B_1$ determined based on a slowly rising maximum volume-maximum steam curve, the generated steam volume is smaller than in the case of a food having a maximum weight. Therefore, it can be judged that heating is performed in a no-load condition with an exceedingly small generated steam volume, and the operation of the heating cooking apparatus is forcedly stopped. When a generated steam volume at a maximum detection time $T_{m+1}$ does not reach a standard steam volume A determined based on the maximum volume-maximum steam curve, it is judged that a large amount of food exceeding a maximum amount is being heated and the operation of the heating cooking apparatus is forcedly stopped.

9 Claims, 5 Drawing Sheets

U.S. PATENT DOCUMENTS

| | | | | | |
|---|---|---|---|---|---|
| 5,459,303 | A | * | 10/1995 | Kwon | 219/705 |
| 5,464,967 | A | * | 11/1995 | Gong | 219/703 |
| 5,496,576 | A | * | 3/1996 | Jeong | 426/233 |
| 5,545,881 | A | * | 8/1996 | Chai et al. | 219/719 |
| 5,681,496 | A | * | 10/1997 | Brownlow et al. | 219/707 |
| 5,689,060 | A | * | 11/1997 | Matsushima | 73/24.04 |
| 5,889,264 | A | * | 3/1999 | Kidblad et al. | 219/707 |

FOREIGN PATENT DOCUMENTS

JP 2003-214632 A 7/2003

* cited by examiner

METHOD OF CONTROLLING HEATING COOKING APPARATUS

1. BACKGROUND OF THE INVENTION

1. Field of the Invention

The present invention relates to a method of controlling a heating cooking apparatus, such as a drawer-type microwave oven in which a drawer body on which a food to be heated is placed can be withdrawn from a cooking-apparatus main body.

2. Description of the Related Art

It is commonly known that microwave cooking is prone to overcooking without some smart cooking sensors.

Weight sensor was among the earliest cooking sensors for microwave cooking, which adjusts the cooking duration according to the food weight.

Although weight sensors were used to be the most popular, and are still pretty popular, among the microwave ovens with turntables, it is regarded impossible to implement a weight sensor in drawer type microwave ovens at a reasonable cost because the cooking chamber draws out and in from the microwave oven main body before and after the microwave cooking respectively; other sensing measures must be considered in the preserve of drawer-type microwave ovens.

Humidity cooking sensors detect the floating vapor coming from the foods being cooked, emitting timidly at first and fluently later on when water in the foods starts boiling actively.

Thus, by monitoring cooking chamber humidity continuously by a single humidity sensor, it is economically feasible to detect the state of cooking of various foods in various quantities by the humidity and its dependency during cooking process.

The present invention provides a brand-new and practical management system of humidity sensor to realize both smart cooking duration control and countermeasures against overcooking by implementing a few check points within the humidity sensing and cooking duration control program in drawer-type microwave ovens as calculated upon data from abundant cooking efforts in our laboratories.

FIG. 5 is a perspective view of a heating cooling apparatus of a conventional construction, and FIG. 6 is a side view of the heating cooking apparatus shown in FIG. 5. The heating cooking apparatus shown in FIGS. 5 and 6 is provided with a cooking-apparatus main body 1 having a heating chamber 3 for the heating cooking of an object to be heated and a drawer body 2 that can be pushed into and pulled out of the cooking-apparatus main body 1. The drawer body 2 has an opening and closing door 6 for opening and closing the heating chamber 3 and a heating receptacle 7 for housing an object to be heated by placing the object to be heated thereon. The drawer body 2 is disposed so as to be movable within the cooking-apparatus main body 1 in such a manner that the drawer body 2 can be withdrawn to the front side from within the heating chamber 3 of the cooking-apparatus main body 1. A moving mechanism 4 for moving the drawer body 2 within the cooking-apparatus main body 1 is constructed as a sliding mechanism using rails. The heating receptacle 7 has side walls on the right and left sides, a back wall on the back side that is disposed within the heating chamber 3 of the cooking-apparatus main body 1, and an opening that opens upward, and is provided with the opening and closing door 6 at the front. When the opening and closing door 6 closes the opening of the heating chamber 3, the inner space of the heating chamber 3 becomes an enclosed space formed by the inner wall surfaces of the cooking-apparatus main body 1 and the drawer body 2 and is configured to prevent microwaves, which are radiated to the interior of the heating chamber 3 to heat an object to be heated, from leaking.

The opening and closing door 6 of the drawer body 2 is supported on the cooking-apparatus main body 1 by the right and left side wall positioned outside the heating chamber 3 via the moving mechanism 4. The moving mechanism 4 is constituted by a fixed rail 9 and a moving rail 8 made of an angle, which slides along the fixed rail 9. The fixed rail 9 is attached to the right and left side walls of the heating chamber 3 of the cooking-apparatus main body 1 outside the heating chamber 3. The moving rail 8 is attached to the inner wall surface of the opening and closing door 6 via metal fittings so as to extend from the inner wall surface of the opening and closing door 6 of the drawer body 2 toward the interior of the heating chamber 3 of the cooking-apparatus main body 1. Because the moving mechanism 4 is provided outside the heating chamber 3, it is unnecessary to use expensive parts or materials having high heat resistance and flame resistance in fabricating the moving rail 8 and the fixed rail 9, and there is no fear that the moving rail 8 and the fixed rail 9 might be affected by microwaves radiated to the interior of the heating chamber 3, nor is there any fear of discharges by microwaves. A driving mechanism for driving the moving mechanism 4, though not shown in the figures, has a DC motor and a transmission mechanism coupled to a rotational output shaft of the DC motor, such as gears, and a pinion positioned in the last stage of the transmission mechanism has a meshing engagement with a rack attached to the moving rail 8. The drawer body 2 can be pushed into and pulled out of the cooking-apparatus main body 1 by rotating the pinion through the output of the DC motor.

Compared to general stationary microwave ovens, thanks to the characteristics of the drawer construction, many drawer-type heating cooking apparatus, such as microwave ovens, are constructed to have a flat shape with a wide bottom surface in the interior of the heating chamber 3 inside the heating-cooking apparatus, and with a small height. Therefore, a large amount of food can be placed within the heating chamber 3 because of the wide bottom surface area for the inside capacity, and it can be said that changes in the amount of the placed food are greater than in the stationary type.

In heating cooking apparatus such as microwave ovens, there has been publicly known an automatic cooking sequence that involves providing a humidity sensor that detects steam in the heating chamber 3, detecting that the generation of steam becomes active as the food temperature rises during the progress of heating cooking, and judging the progress status of heating cooking.

In automatic heating cooking apparatus using such a humidity sensor as described above, a detection point (a steam volume) is determined according to the manner in which steam is generated, which depends on the kinds of foods, and the heating time elapsing from the detection point until the finish of cooking is determined on the basis of the time that elapses from the start of heating to the detection point.

Also, it has been publicly known that an abnormal state, such as a case where heating processing is performed under no load, that is, without the presence of an object to be heated, is detected by using the functions of a humidity sensor. That is, this technique has a safety mechanism by which it is judged that an abnormal state, such as a no-load state, has occurred when a prescribed humidity is not detected by a given time after the start of heating cooking and long-time heating is avoided by forcedly finishing the heating when steam is not detected by a given time according to menus.

By inputting information on the weight of food using a weight sensor in automatic heating cooking using a humidity sensor, it is possible to adjust the heating time that elapses from a detection point to the finish of cooking according to changes in the amount of food. However, in a microwave oven not using a turn table, which is a rotary placement table, for structural reasons it is difficult to incorporate a weight sensor. Because of cost constrains, generally, a weight sensor is not built in microwave ovens of prevailing price whose functions are narrowed down to microwave heating.

Even when only a humidity sensor is used, by adjusting control conditions according to the kinds of foods, it is possible to perform substantially accurate automatic cooking for a given amount of food, but it is difficult to automatically adapt to variations in the amount of food. If conditions are set on the basis of a case where the amount of food is large, there is a possibility of overheating when the amount of food is small. Conversely, if conditions are set on the basis of a case where the amount of food is small, there is a possibility that heating becomes insufficient when the amount of food is large.

For the above-described structural reason, it can be said that drawer-type heating cooking apparatus have a wide weight range of placed food and that the weight range tends to vary. Furthermore, also the distance between the position where a food is placed and the humidity sensor is apt to vary and hence the detection accuracy of the humidity sensor tends to vary. Also, because drawer-type microwave ovens generally do not use a turn table, which is a rotary placement table, variations in the distance between the position where a food is placed and the humidity sensor are not averaged. Therefore, the distance from the humidity sensor is apt to vary according to the manner in which a food is placed within the heating chamber 3, and cooking results tend to vary in the case of automatic cooking using the humidity sensor.

It is possible to reduce variations in the results of automatic cooking by increasing the number of humidity sensors and detecting the humidity at a plurality of points of the heating chamber. However, because the number of humidity sensors to be installed increases in order to cope with all situations by various kinds of heating states of food, the manufacturing cost of heating cooking apparatus rises and problems such as complex control programs occur.

There has been proposed a method of preventing abnormal heating that involves measuring variations in the weight of an object to be heated during heating thereof by use of weight measuring means (a weight sensor), calculating an abnormal heating judgment weight by a calculation formula set beforehand by abnormal heating judgment weight calculating means on the basis of high frequency outputs and the time that elapses from the start of heating to the detection of steam by a humidity sensor, comparing this abnormal heating judgment weight with a weight loss of the object to be heated, and detecting an abnormally heated state from that fact that the weight loss has reached the abnormal heating judgment weight (Japanese Patent Laid-Open Publication No. 2003-214632).

Also, there has been proposed a method that involves providing an absolute temperature sensor that detects the temperature of exhaust air from a heating chamber as absolute temperature in the vicinity of an exhaust air port of a microwave oven, judging the heated state of an object to be heated within the heating chamber on the basis of detection outputs of this sensor, and detecting abnormal heating thereby (Japanese Patent Laid-Open Publication No. 62-126589).

Therefore, there are problems to be solved in an aspect that involves beforehand determining a heating time from the start of heating and a critical steam volume during this time on the basis of a steam curve that fixes a relationship between heating time and a generated steam volume, and detecting an abnormally heated state of the object to be heated, such as a no-load heating condition and a heated state which is such that a maximum volume is exceeded, on the basis of an actual heating time of an object to be heated and a generated steam volume.

SUMMARY OF THE INVENTION

The object of the present invention is to provide a method of controlling a heating cooking apparatus that involves accurate heating processing of food by one sequence and can prevent even underheating while avoiding overheating by using only a humidity sensor if the food has a weight within a given weight range, even in the case of a heating cooking apparatus that cannot use a weight sensor, such as a microwave oven.

To solve the above problems and achieve the above object, the method of controlling a heating cooking apparatus according to the present invention is a method of controlling a heating cooking apparatus that involves judging the progress status of heating cooking by detecting a steam volume in a heating chamber by use of a humidity sensor. In this control method, the operation of the heating cooking apparatus is forcedly stopped by responding to the fact that a generated steam volume at a forced finish time found on the basis of a minimum amount-minimum steam curve for a food having a minimum weight does not reach a minimum steam volume found on the basis of the forced finish time and a maximum amount-maximum steam curve for a food having a maximum weight.

According to this method of controlling a heating cooking apparatus, a minimum amount-minimum steam curve for a food having a minimum weight is a quickly rising curve compared to a maximum amount-maximum steam curve for a food having a maximum weight. Therefore, when a generated steam volume at a forced finish time found on the basis of the minimum amount-minimum steam curve does not reach even a minimum steam volume found on the basis of the forced finish time and the slowly rising maximum amount-maximum steam curve, the generated steam volume is smaller than in the case of a food having a maximum weight. Accordingly, it can be judged that the food is not housed in the heating chamber and that heating is performed in a no-load state with an extremely small generated steam volume, and the operation of the heating cooking apparatus is forcedly stopped, whereby it is possible to cope with this abnormal situation. In this case, because the judgment is based on the condition that the generated steam volume does not reach even a minimum steam volume found on a the basis of maximum amount-maximum steam curve, it is possible to avoid misjudging that the generated steam volume decreased due to the placing of a maximum amount of food.

In this method of controlling a heating cooking apparatus, the forced finish time can be a time that is obtained by subtracting a time obtained in consideration of a safety factor provided for food conditions from a time that elapses until the food having a minimum weight comes to an overheated state in the minimum amount-minimum steam curve, when the food is placed under the condition which is such that the food having a minimum weight comes to an overheated state earliest. According to this control method, the forced finish time is fixed by subtracting a time obtained in consideration of a safety factor from the time that elapses until the food having a minimum weight comes to an overheated state earliest.

Therefore, for a minimum steam volume found from the maximum amount-maximum steam curve, a value obtained at a stage earlier than the time that elapses until the food having a minimum weight domes to an overheated state is used and, therefore, it is possible to make a judgment, at an early stage, as to whether or not the operation of the heating cooking apparatus should be forcedly stopped.

In this method of controlling a heating cooking apparatus, the minimum steam volume is determined as a steam volume smaller than a steam volume obtained at the forced finish time in the maximum amount-maximum steam curve in consideration of a safety factor provided for food conditions. Because the minimum steam volume can be thus determined as a steam volume smaller than a steam volume found from maximum amount-maximum steam curve in consideration of a safety factor, a careful judgment is made as to whether or not the operation of the heating cooking apparatus should be forcedly stopped by using a steam volume of a lower value and, therefore, it is possible to prevent a wrong forced stop of the operation of the heating cooling apparatus.

In this method of controlling a heating cooking apparatus, a maximum detection time is set on the basis of a detection time that elapses until a standard steam volume is reached when the food having a maximum weight is placed under a condition of the latest detection time, and the operation of the heating cooking apparatus can be forcedly stopped when a generated steam volume at the maximum detection time does not reach the standard steam volume. When an amount of food having a weight of not less than a maximum weight is heated, a temperature rise becomes insufficient and a generated steam volume decreases. According to this control method, when a generated steam volume at the maximum detection time does not reach the standard steam volume, it is judged that a food having a weight of not less than a maximum weight is housed in the heating chamber, and the operation of the heating cooking apparatus is forcedly stopped.

In the method of controlling a heating cooking apparatus used in heating a food having a maximum weight, the maximum detection time can be a time that is obtained by adding a time obtained in consideration of a safety factor provided for food conditions to the detection time in the maximum amount-maximum steam curve. That is, for the detection time that corresponds to a standard steam volume in the maximum amount-maximum steam curve, a time which elapses by the time amount obtained by taking a safety factor into consideration is regarded as the maximum detection time. Therefore, a careful judgment is made by spending more time as to whether or not the operation of the heating cooking apparatus should be forcedly stopped and, therefore, it is possible to prevent a wrong forced stop of the operation of the heating cooling apparatus.

In this method of controlling a heating cooking apparatus, the heating cooking apparatus can be a drawer-type heating cooking apparatus in which a drawer body on which an object to be heated is placed can be withdrawn from a cooking-apparatus main body. In drawer-type heating cooking apparatus, the floor area of the heating chamber is set wide although the height is small and, therefore, the difference between a minimum amount and a maximum amount of the placed food becomes apt to increase. However, according to this method of controlling a heating cooking apparatus, even when variations occur in the detection by a humidity sensor due to the positions of the placed food, it is possible to perform automatic cooking by avoiding overheating in the case of a small amount while avoiding underheating in the case of a large amount. Also, there is realized a cooking sequence that finishes heating in a short time and can prevent small-scale overheating in the event of a sensor abnormality.

In the foregoing, the description was given of two kinds of vapor volumes (a minimum vapor volume and a standard vapor volume) and detection times (a forced finish time and a maximum detection time) that become critical values during heating cooking. However, it is more preferable to provide a judgment point for judging conditions at the midpoint of each critical value, because this enables cooking time to be more accurately controlled to adapt to changes in the amount of placed food.

Also, it is more preferable to judge conditions by using time-series data at a multiple of continuous points, because this enables the effect of detection errors due to noise to be avoided.

For a safety factor, it is more preferable to conduct cooking experiments under various kinds of food conditions and to adjust the safety factor according to tendencies toward variations in the kinds of foods, cooking methods and the like, because this can increase the accuracy of heating time control in actual use.

DETAILED DESCRIPTION OF THE INVENTION

Figure 1:
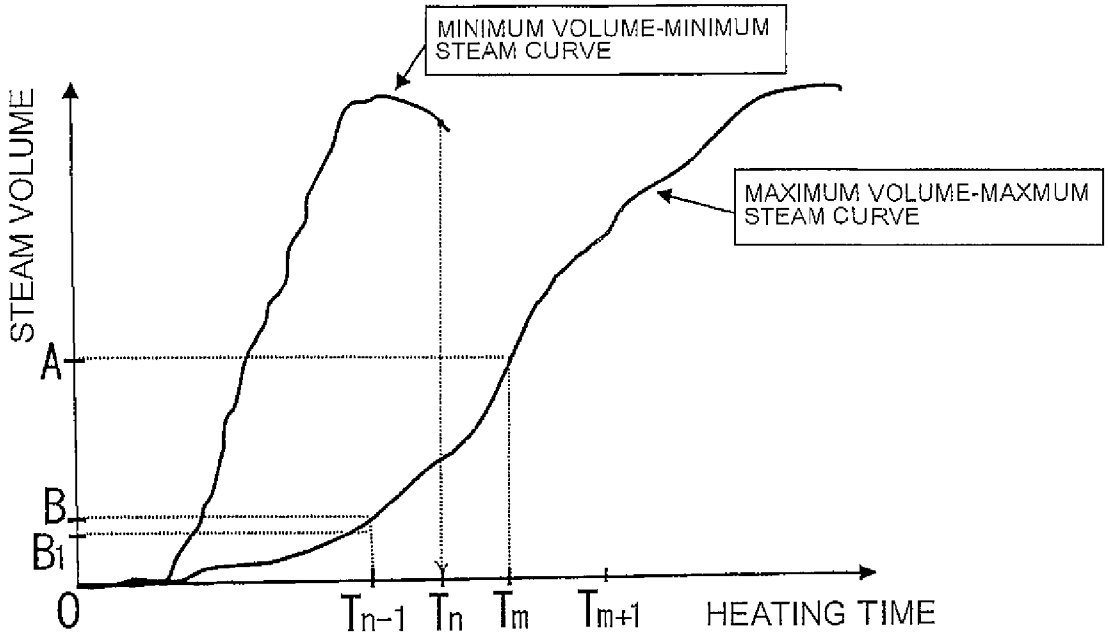
FIG. 1 is a diagram showing a critical steam curve in a method of controlling a heating cooking apparatus related to the present invention.
Figure 5:
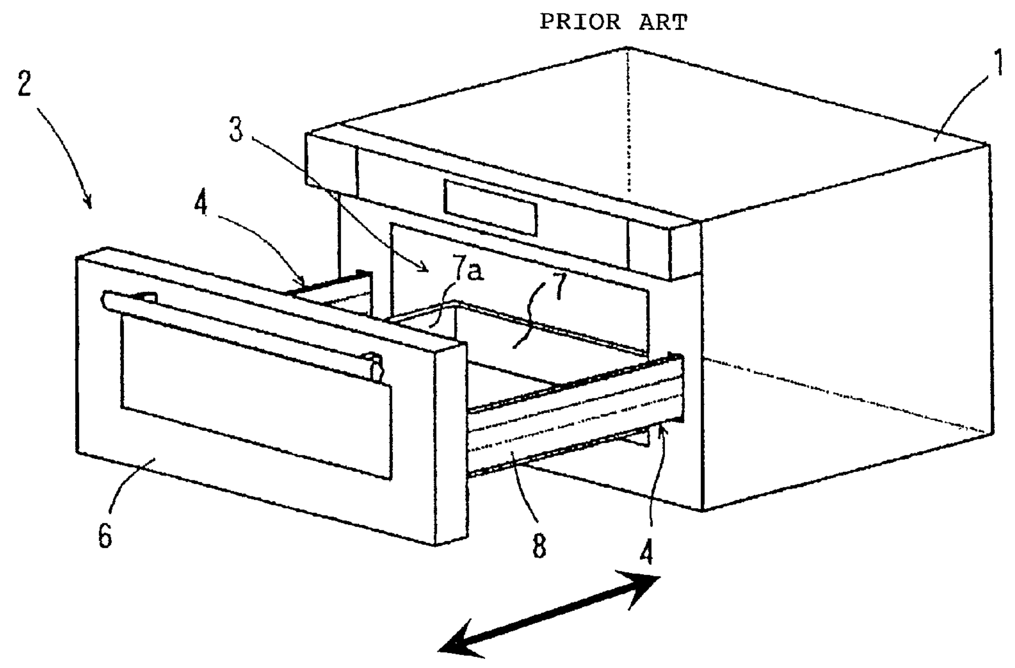
FIG. 5 is a perspective view of a conventional drawer-type heating cooking apparatus.
Figure 6:
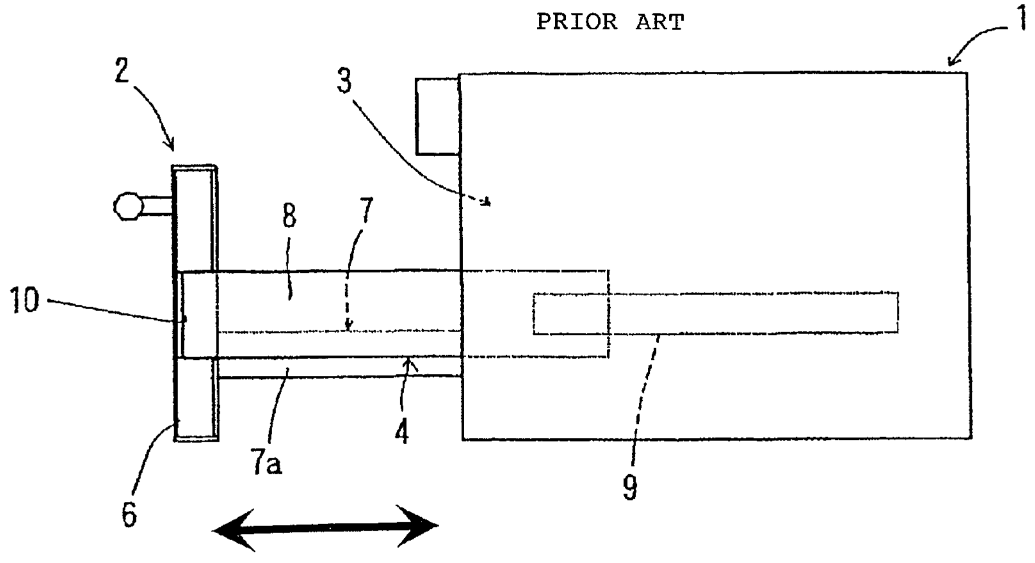
FIG. 6 is a side view of the drawer-type heating cooking apparatus shown in FIG. 5.

Next, an embodiment of the method of controlling a heating cooking apparatus according to the present invention will be described with reference to the accompanying drawings. FIG. 1 is an example of a graph showing changes in steam volume that occur every moment for the heating time obtained by the control of the heating cooking apparatus according to the present invention. The heating cooking apparatus to which this control method can be applied can be a drawer-type heating cooking apparatus provided with a drawer body on which an object to be heated is placed and which is capable of being withdrawn together with a door. The drawer-type heating cooking apparatus shown in FIGS. 5 and 6, for example, may also be adopted, and an overlapping description thereof is omitted.

As shown with reference to a maximum amount-maximum steam curve in FIG. 1, a maximum detection time $T_{m+1}$ is set as a time obtained by adding a time obtained in consideration of a safety factor provided for food conditions (changes such as a difference in the water content of food due to seasons and production areas and a difference in shape and initial temperature) to a detection time that elapses when a food having a maximum weight is placed under a condition which is such that the detection time becomes longest (a time that elapses until a standard steam volume A is reached) $T_m$ with reference to an automatic cooking sequence that covers a given weight range (an additional heating time after detection is calculated from a time that elapses until a given steam volume is detected).

Similarly, as shown with reference to a minimum amount-minimum steam curve in FIG. 1, a forced finish time $T_{n-1}$ is set as a time $T_n$ obtained by subtracting a time obtained in consideration of a safety factor provided for food conditions from a time that elapses until the food having a minimum weight comes to an overheated state (a state obtained when a prescribed time elapses after the steam volume curve begins to decline after peaking) when the food is placed under the condition which is such that the food having a minimum weight comes to an overheated state earliest.

For a steam volume B at a time $T_{n-1}$ in a case where a food having a maximum weight is placed under a condition which is such that the detection time becomes longest (the maximum amount-maximum steam curve of FIG. 1), a minimum vapor volume $B_1$ is set in consideration of a safety factor provided for food conditions. At this time, the following relationship holds: $B_1<B<A$.

Figure 2:
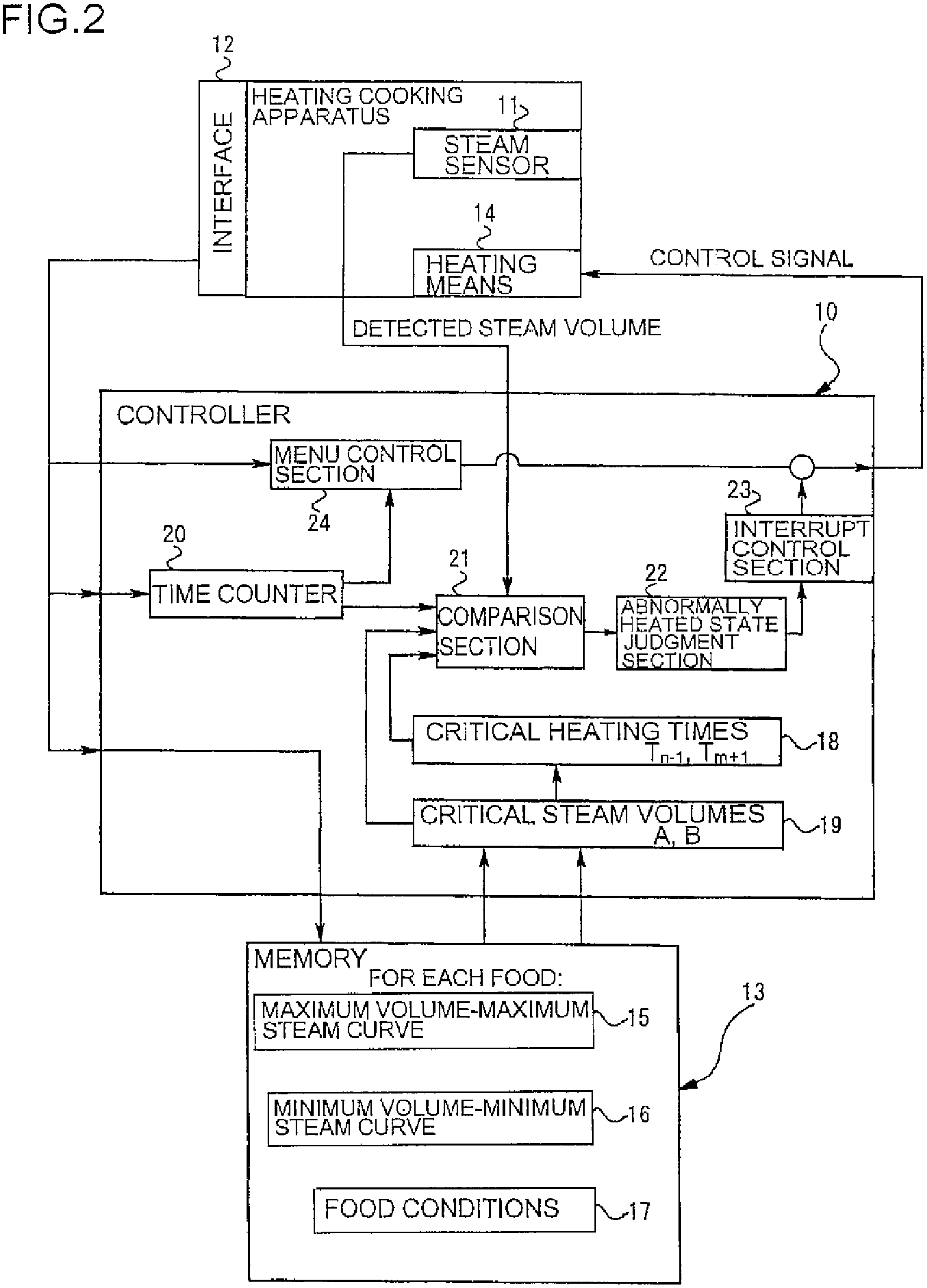
FIG. 2 is a block diagram of the control method of the present invention.

FIG. 2 is a block diagram showing how the control method of a heat cooking apparatus according to the present invention is executed. The control block is provided with a controller 10 constituted by a microcomputer, a steam sensor 11 that is disposed in the cooking-apparatus main body 1 and detects the steam volume in the heating chamber 3, an interface section 12 where various kinds of settings and operations in the heating cooking apparatus are performed, a memory 13 that stores data necessary for the execution of the method of controlling a heating cooking apparatus, and heating means (concretely, microwave generating means) 14 whose degree of heating and stop of heating are controlled by receiving a control signal output by the controller 10 on the basis of a steam volume detected by the steam sensor 11.

At least a maximum amount-maximum steam curve 15, a minimum amount-minimum steam curve 16 and food conditions 17 shown in FIG. 1 are stored in a memory 13 according to the kinds of foods. On the basis of these data and on the basis of the operation of menu buttons in the interface section 12, critical heating times 18 such as a forced finish time $T_{n-1}$ and a maximum detection time $T_{m+1}$ and critical steam volumes 19 such as a standard steam volume A and a steam volume $B_1$ are set in the controller 10. Also in the controller 10, a time counter 20 ticks a heating time on the basis of the operation of a heating start button in the interface section 12.

In the case of ordinary heating, on the basis of the operation of menu buttons in the interface section 12, control by a menu control section 24 is executed on the basis of a heating time signal from the time counter 20, and a control signal is output to the heating means 14. On the other hand, in order to forcedly stop the heating means 14 by detecting an abnormally heated state, such as a no-load heating condition and overweight, a signal of a detected steam volume from the steam sensor 11, signals of set critical heating time 18 and critical steam volume 19, and a heating time signal from the time counter 20 are sent to a comparison section 21. In the comparison section 21, a comparison between a detected steam volume and a critical steam volume 19 is made at each of the critical heating times 18, and on the basis of the result of the comparison an abnormally heated state judgment section 22 makes a judgment as to whether or not the heated state is an abnormally heated state. If the judgment result is an abnormally heated state, an interrupt control section 23 interrupts ordinary menu control and performs control to forcedly stop the heating means 14.

Figure 3:
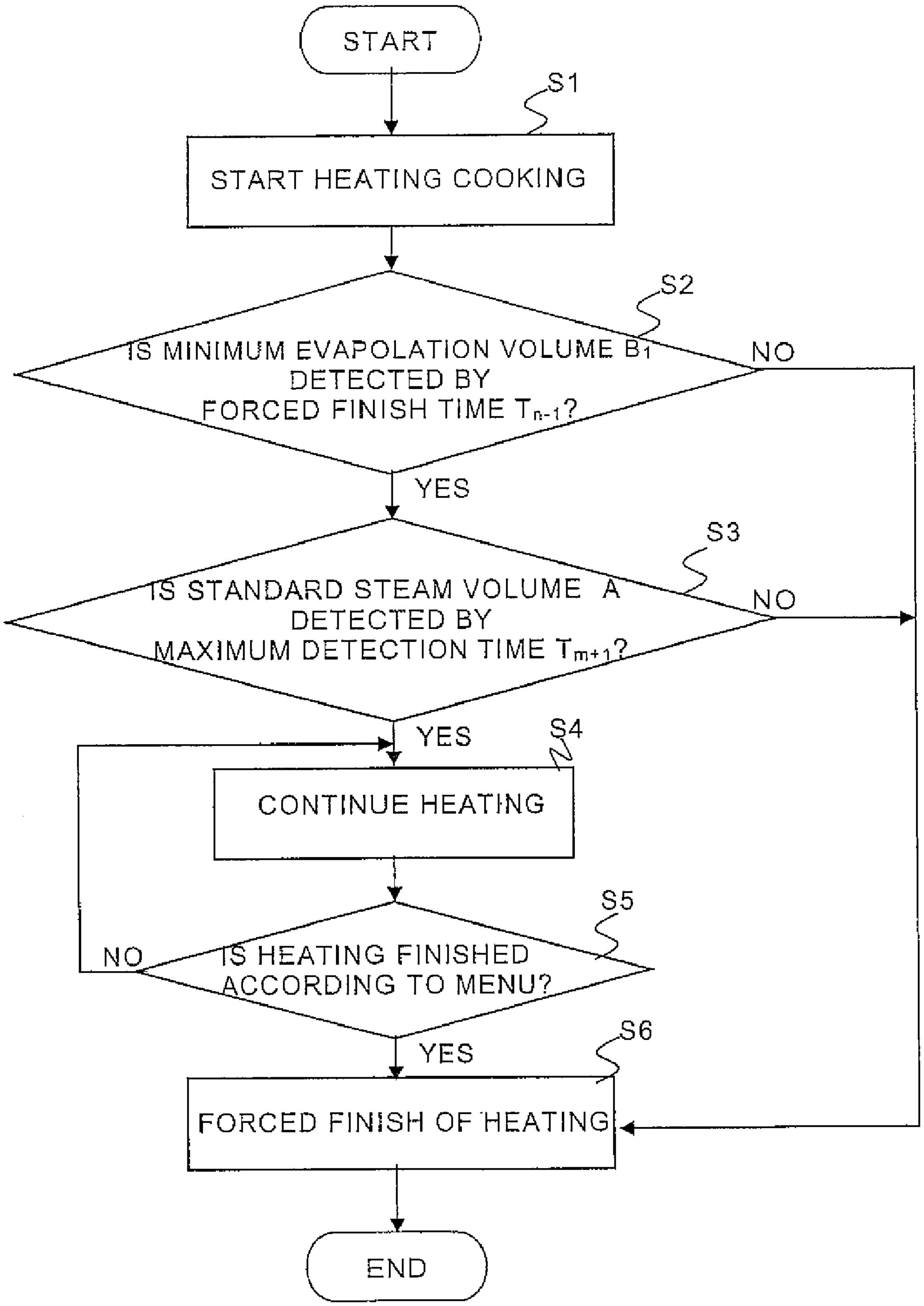
FIG. 3 is a flowchart of the control method of the present invention.

Heating control of an object to be heated in the heating cooking apparatus is performed under the above-described conditions. FIG. 3 is a flowchart showing an example of the method of controlling a heating cooking apparatus according to the present invention. After the start of heating cooking (Step 1, abbreviated as "S1," the same applies to the following), a judgment is made as to whether or not a minimum steam volume $B_1$ is detected by a forced finish time $T_{n-1}$ (S2). When the minimum steam volume $B_1$ is not detected, it is judged that a food to be heated or the like is not placed in the heating chamber, that is, heating in a no-load condition is performed, and heating is forcedly finished at this point in time (S6).

When a minimum steam volume $B_1$ has been detected in Step 2, a judgment is further made as to whether or not a standard vapor volume A is detected by a maximum detection time $T_{m+1}$ (S3). When the standard vapor volume A is not detected in S3, it is judged that an object to be heated or the like has an overweight exceeding a maximum amount and that this is abnormal heating from which a sufficient temperature rise cannot be obtained, and the heating is forcedly finished at this point in time (S6). When a standard vapor volume A has been detected in S3, ordinary heating is continued (S4). A judgment is made as to whether or not conditions for the finish of heating according to menus are satisfied (S5), the heating is continued unless the conditions for the finish are satisfied (S4), and if the conditions for the finish are satisfied, the heating is finished at this point in time (S6).

When the above-described control is performed, in a heating cooking apparatus in which the difference between a minimum amount and a maximum amount of placed food is great, and also in a case where variations occur in the detection by a humidity sensor due to the position of placed food, it is possible to perform automatic cooking capable of avoiding overheating in the case of a small amount while avoiding underheating in the case of a large amount. Also, there is realized a cooking sequence that can finish heating in a short time in the event of a sensor abnormality.

Thus, even in a heating cooking apparatus for which a weight sensor cannot be adopted due to constrains in cost and structure, it is possible to perform accurate heating cooking using only a humidity sensor.

In the foregoing, as representative heating points, description was given of two kinds of heating times and vapor volumes that become critical values during heating cooking. However, in addition to these heating points, it is more preferable to provide one or more judgment points for judging conditions at the midpoint of each critical value on the basis of these steam curves, because this enables cooking time to be more accurately controlled to adapt to changes in the amount of placed food. Also, it is more preferable to judge conditions by using time-series data at a multiple of continuous points, because this enables the effect of detection errors due to noise to be avoided.

For a safety factor that determines critical values, it is more preferable to conduct cooking experiments under various kinds of food conditions and to adjust the safety factor according to tendencies toward variations in the kinds of foods, cooking methods and the like, because this can increase the accuracy of heating time control in actual use. In this embodiment, because a judgment is made as to whether or not a detected steam volume at a forced finish time $T_{n-1}$ determined on the basis of a minimum volume-minimum steam curve reaches a minimum steam volume $B_1$, it is possible to detect heating in the absence of an object to be heated, i.e., a no-load heating condition, at an early stage of heating time. In addition, because a minimum steam volume $B_1$ is set on the basis of a maximum steam volume for a maximum amount within an ordinary weight range, there is no possibility of continuing no-load heating by making a wrong judgment that the steam volume occurs in a case where the weight of an object to be heated is heavy in an ordinary weight range.

The above description was given of a control method of heating cooking apparatus in general. However, in the case of a drawer-type heating cooking apparatus, such as a drawer-type microwave oven, the heating chamber has a flat shape and an object to be heated tends to be placed and housed in a larger amount than in the case of a stationary cooking apparatus and, therefore, weight variations and detection variations due to the installation place of the steam sensor 11 are apt to occur. According to the control method of the present invention, it is possible to accurately cope with such variations and to perform heating control.

Figure 4:
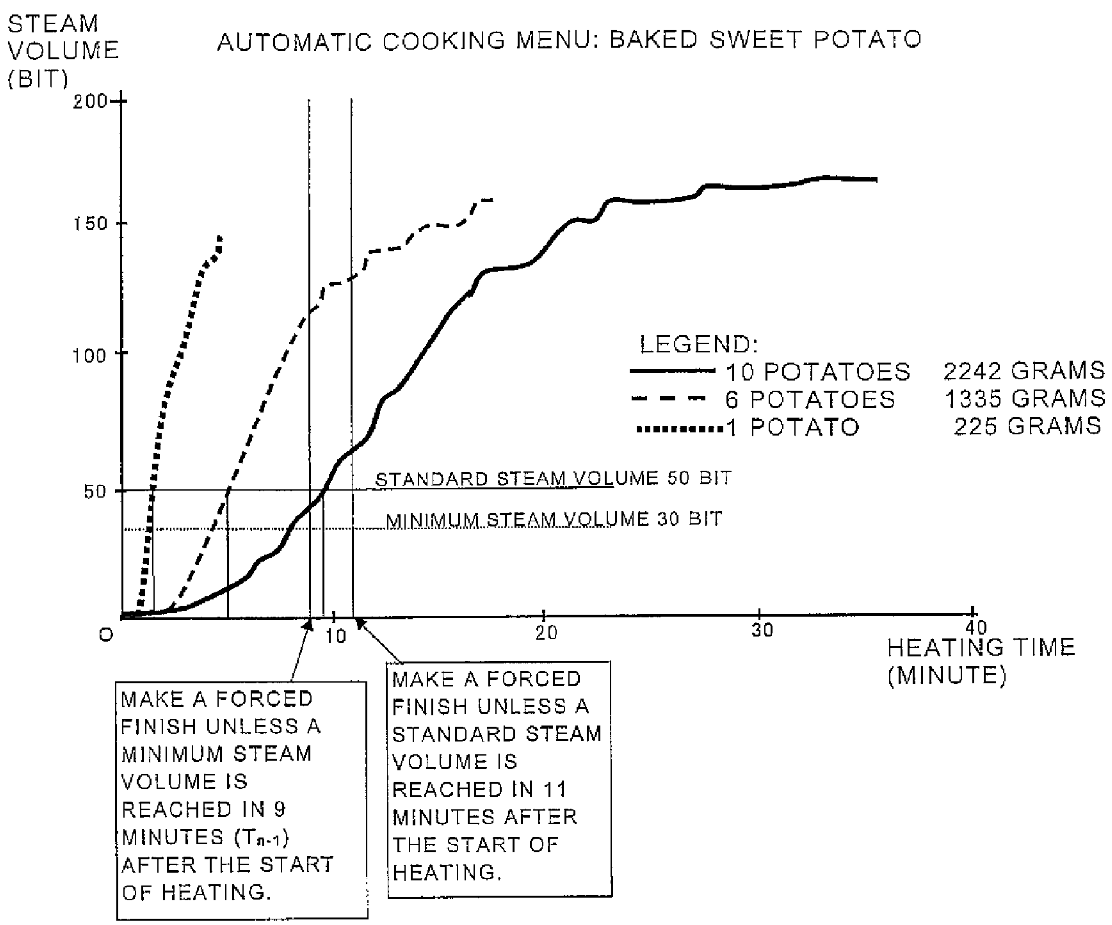
FIG. 4 is a graph showing experimental data of the present invention.

FIG. 4 shows cooking experiment data of a drawer-type microwave oven in which the control method of the present invention is adopted.

In the method of controlling a heating cooking apparatus according to the present invention, a steam volume is detected at each point during a lapse of heating time and heating is forcedly finished as required, whereby in one automatic cooking sequence that covers a given weight range (an additional heating time after detection is calculated from a time that elapses until a given steam volume is detected), it is possible to prevent underheating while preventing overheating regardless of the weight even in a case where foods having different weights are heated each time heating is performed.

Although an abnormality in the sensor itself can be detected by performing self-check immediately after the start of heating, according to the present invention, it is possible to prevent overheating during the heating of food also in the case of an abnormality in the installation of the sensor and the like.

As described above, even in a heating cooking apparatus for which a weight sensor cannot be adopted due to constrains in cost and structure, such as a microwave oven, it is possible to perform accurate heating processing of food by one sequence and to prevent even underheating while preventing overheating by using only a humidity sensor if the food has a weight within a given weight range.

What is claimed is:

1. A method of controlling a heating cooking apparatus comprising:

judging a progress status of heating cooking by detecting a steam volume in a heating chamber of the heating cooking apparatus by a humidity sensor;

providing at least two check points, including a first predetermined time and a second predetermined time longer than the first predetermined time, for making a decision as to whether the heating cooking should be continued or stopped based on the detected steam volume at a point in time when a heating cooking time has elapsed; and stopping the heating cooking (a) when the detected steam volume at the first predetermined time has not reached a first prescribed steam volume; and (b) when the detected steam volume at the second predetermined time exceeds a second prescribed steam volume larger than the first prescribed steam volume.

2. The method of controlling a heating cooking apparatus according to claim 1, wherein the first predetermined time is a forced finish time that is obtained on the basis of a minimum steam curve for a food having a minimum weight and wherein the first prescribed steam volume is a minimum steam volume found on the basis of the forced finish time and a maximum steam curve for a food having a maximum weight.

3. The method of controlling a heating cooking apparatus according to claim 2, wherein the forced finish time is a time that is obtained by subtracting a time obtained in consideration of a safety factor provided for food conditions from a time that elapses until the food having a minimum weight comes to an overheated state in the minimum steam curve, when the food is placed under the condition which is such that the food having a minimum weight comes to an overheated state earliest.

4. The method of controlling a heating cooking apparatus according to claim 2, wherein the minimum steam volume is determined as a steam volume smaller than a steam volume obtained at the forced finish time in the maximum steam curve in consideration of a safety factor provided for food conditions.

5. The method of controlling a heating cooking apparatus according to any one of claims 1 to 4, wherein the heating cooking apparatus is a drawer-type heating cooking apparatus in which a drawer body on which an object to be heated is placed can be withdrawn from a cooking-apparatus main body.

6. The method of controlling a heating cooking apparatus according to any one of claims 1 to 4, wherein the second predetermined time is a maximum detection time based on a detection time that elapses until a standard steam volume is reached when a food having a maximum weight is placed under conditions of the latest detection time and wherein the second prescribed steam volume is the standard steam volume.

7. The method of controlling a heating cooking apparatus according to claim 6, wherein the heating cooking apparatus is a drawer-type heating cooking apparatus in which a drawer body on which an object to be heated is placed can be withdrawn from a cooking-apparatus main body.

8. The method of controlling a heating cooking apparatus according to claim 6, wherein the maximum detection time is a time that is obtained by adding a time obtained in consideration of a safety factor provided for food conditions to the detection time.

9. The method of controlling a heating cooking apparatus according to claim 8, wherein the heating cooking apparatus is a drawer-type heating cooking apparatus in which a drawer body on which an object to be heated is placed can be withdrawn from a cooking-apparatus main body.

* * * * *